United States Patent [19]

Bertellini et al.

[11] 4,403,992
[45] Sep. 13, 1983

[54] CONTINUOUS PERITONEAL DIALYSIS BAG DEVICE

[75] Inventors: Gianfranco Bertellini, Maslianico; Luigi Fabbri, Bologna, both of Italy

[73] Assignee: Sis-Ter S.p.A., Pignano, Italy

[21] Appl. No.: 307,386

[22] Filed: Oct. 1, 1981

[30] Foreign Application Priority Data

Oct. 6, 1980 [IT] Italy .................. 25139 A/80

[51] Int. Cl.³ .................... A61M 5/14; A61M 1/03
[52] U.S. Cl. ................... 604/410; 604/29; 604/80; 604/82; 604/262
[58] Field of Search ............. 128/272, 272.1, 213 A, 128/213 R, 214 D, 247, 227, 214 C, 214 G, 214.2, 272.3, DIG. 24; 150/DIG. 1, 2.1, 2.5, 8; 206/05, 222; 222/94, 145, 107, 129; 604/29, 80–83, 89, 91, 262, 410, 56

[56] References Cited

U.S. PATENT DOCUMENTS

| 2,853,069 | 9/1958 | Beacham et al. |
| 3,127,892 | 4/1964 | Bellamy et al. ............ 128/DIG. 24 |
| 3,182,728 | 5/1965 | Zabriskie ................. 128/DIG. 24 |
| 3,187,750 | 6/1965 | Tenczar, Jr. ................... 604/410 |
| 3,197,071 | 7/1965 | Kuster ........................... 222/94 |
| 3,257,072 | 6/1966 | Reynolds . |
| 3,635,375 | 1/1972 | Gaetke . |
| 3,756,237 | 9/1973 | Chittenden . |
| 3,776,775 | 12/1973 | Lazarus . |
| 3,911,918 | 10/1975 | Turner .................. 128/214 D X |
| 3,921,634 | 11/1975 | Mather et al. ............ 128/DIG. 24 |
| 3,927,671 | 12/1975 | Chittenden et al. . |
| 3,943,929 | 3/1976 | Patel . |
| 4,081,372 | 3/1978 | Atkin . |
| 4,114,617 | 9/1978 | Turner et al. ................ 128/214 G |
| 4,181,140 | 1/1980 | Bayham et al. . |
| 4,191,183 | 3/1980 | Mendelson ............... 128/214 C X |
| 4,198,972 | 4/1980 | Herb ......................... 128/272 X |
| 4,235,230 | 11/1980 | Stephen et al. ............... 604/29 X |
| 4,270,534 | 6/1981 | Adams ......................... 128/247 |
| 4,340,052 | 7/1982 | Dennehey et al. ............ 128/247 |

FOREIGN PATENT DOCUMENTS

| 29526 | 6/1981 | European Pat. Off. . |
| 88515 | 1/1896 | Fed. Rep. of Germany . |
| 7719528 | 3/1978 | Fed. Rep. of Germany . |
| 2853635 | 6/1980 | Fed. Rep. of Germany . |
| 2951106 | 6/1981 | Fed. Rep. of Germany ... 128/214.2 |
| 1404624 | 5/1965 | France . |
| 2312263 | 12/1976 | France ................. 128/214 D |
| 2455462 | 1/1981 | France ................. 128/213 A |
| 1428373 | 3/1976 | United Kingdom ........... 128/214 D |
| 2018720 | 10/1979 | United Kingdom . |
| 2040379 | 8/1980 | United Kingdom . |
| 598067 | 4/1978 | Switzerland . |
| 145313 | 3/1961 | U.S.S.R. . |

OTHER PUBLICATIONS

Proceedings of an International Symposium at Paris, Nov. 2, 3, 1979, "Continuous Ambulatory Peritoneal Dialysis", Excerpta Medica 1980.

Primary Examiner—Richard J. Apley
Assistant Examiner—Michelle N. Lester
Attorney, Agent, or Firm—Frishauf, Holtz, Goodman & Woodward

[57] ABSTRACT

For portable use of peritoneal dialysis, a flexible bag of plastic material has two chambers therein, one being a dialysis liquid chamber (42) and substantially larger than a further disinfectant chamber (8); the bag is formed of thermoplastic material, heat-sealed together at seam lines extending thereacross, and sealed into the seam lines are a communication line (16) from the dialysis chamber (42) to the outside, and a branch duct (17) extending from the disinfectant chamber to the communication duct; the respective ducts are closed off at the inside of the chambers, after filling, by releasable closures, such as a ball squeezed into the duct, or a frangible pin which can be broken off by flexing the bag, thus permitting removal of, respectively, dialysis fluid and disinfectant from the respective chambers; used dialysis fluid can be returned into the bag. The chambers preferably additionally have a penetrable closure, such as a membrane-sealed or sponge-sealed plug, to permit introduction of the respective liquids, thereinto after manufacture. The connection elements, at the outside, are retained in sterile condition by a capsule-like protective element formed of two half-shells filled with sponge material soaked with disinfectant, and releasably connected together.

12 Claims, 4 Drawing Figures

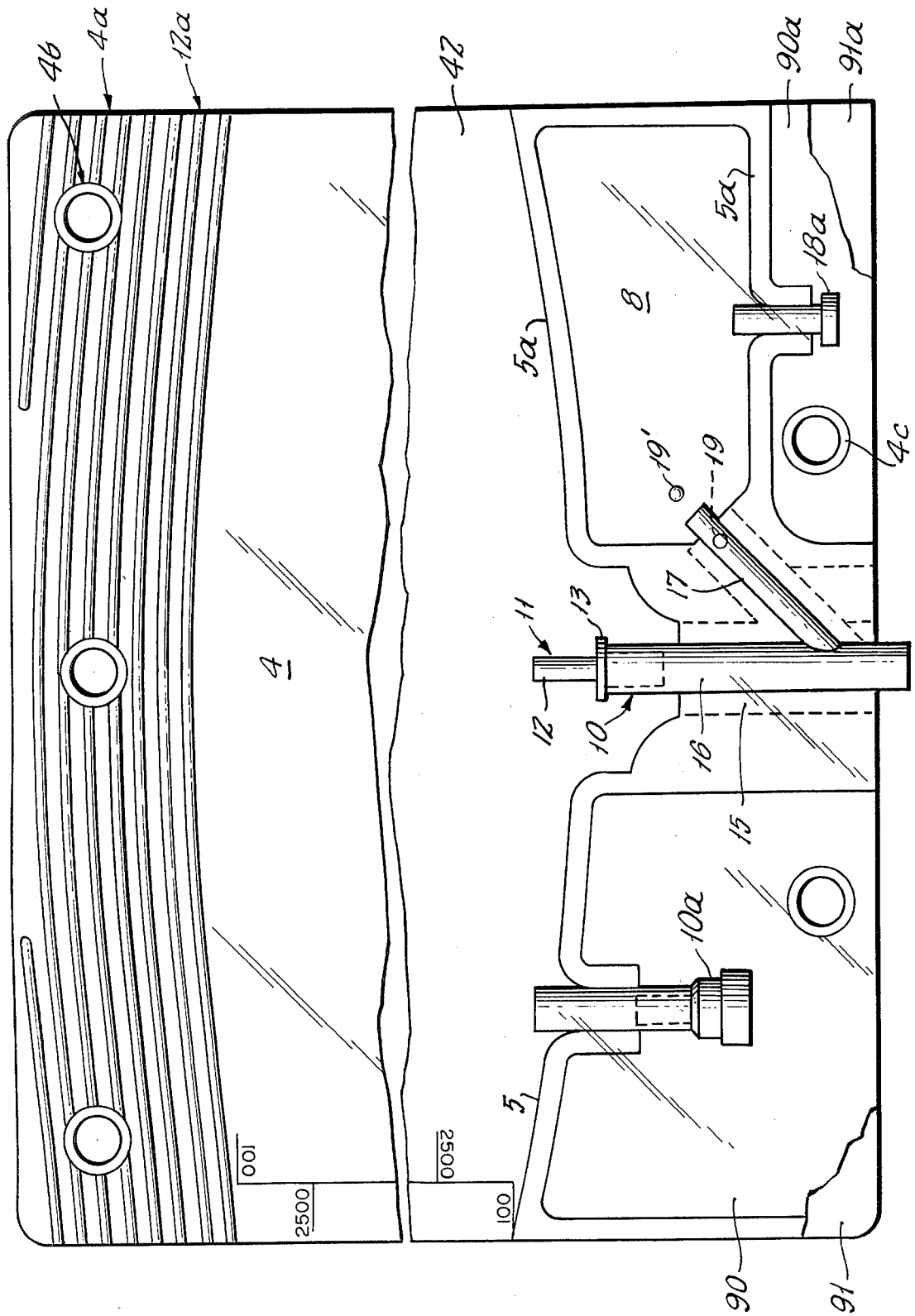

CONTINUOUS PERITONEAL DIALYSIS BAG DEVICE

The present invention relates to continuous dialysis, and more particularly to a bag structure which permits portable use of the bag by a patient, and which is constructed for easy and efficient utilization of dialysis fluid contained therein, or drainage of used fluid thereinto, and for self-use by the patient without medical supervision.

BACKGROUND

Continuous ambulatory peritoneal dialysis, also abbreviated "CAPD", can frequently be used directly by the patient, without medical supervision. Various types of apparatus and systems are known and have been proposed to assist in or completely replace the natural purification functions.

Existing CAPD apparatus have drawbacks, principally due to danger of infection, usually caused by the inevitable contact of the hands of the user with fittings and coupling members which the patient, necessarily, has to handle in a non-sterile environment, even if gloves, adhesive ribbons, and sterilized gauzes are used. Another source of possible infection is due to the possible contamination of dialysis liquid by draining liquid from a preceding dialysis operation. It is practically impossible to eliminate traces of contaminated fluid which are retained in the tubes or fittings of apparatus, and will then be entrained in freshly supplied dialysis liquid for re-introduction into the abdominal cavity, and thus lessening the efficacy on a subsequent dialysis irrigation.

THE INVENTION

It is an object to provide a dialysis liquid containing and receiving bag which is suitable for a single irrigation operation and then to be disposed of, and constructed to permit easy application of the patient for irrigation, while retaining sterility of the apparatus and the coupling elements in connection therewith, and which additionally is constructed to result in a minimum of discomfort to the user with a maximum degree of ease of use.

Briefly, a flexible bag of flexible plastic material is provided which, by seams or sealing walls, is subdivided into two chambers. Preferably, the seams or seals are heat seams formed in two essentially planar, parallel sheets of flexible plastic, such as polyvinyl chloride polymers or the like. A first connection line extends transversely across the bag to define therein a dialysis fluid chamber, in which sterile new dialysis fluid can be introduced. A second connection line, spaced from the first, defines a disinfectant chamber in the bag, which is located, preferably, contiguously to the first chamber and separated merely by the connection line or seam. A communication duct extends from the dialysis fluid chamber to the outside thereof, for connection to a sterile tubing, the connection element of which is protected by a special sterile cap. A second communication duct extends from the disinfectant chamber, merging with the first communication duct from the dialysis chamber, so that, upon permitting dialysis fluid to be introduced into the abdominal cavity of the patient, disinfectant and dialysis fluid can be conjointly introduced. Releasale closure means are connected at least to the second communication duct, preferably formed as plastic plugs with a handle pin which can be broken off from the end portion of the respective communication duct by flexing the respective portion of the bag, so that the disinfectant can reach the fluid flowing from the dialysis bag. The dialysis bag first connection line, preferably, likewise has a similar frangible closure element.

In accordance with a feature of the invention, the respective closure elements have different colors, so that the patient can be given easy instructions with respect to the color coded frangible closure elements which, when broken, permit release of the dialysis fluid and the disinfectant, respectively, from the bag.

The bag, additionally, preferably has further openings, for example in the form of tubes sealed with a penetrable outer seal, to permit introducing the respective fluids into the respective chambers from supplies by injection needles passing through the penetrable closure openings, for example closed off by a thin rubber membrane.

In accordance with a feature of the invention, the end portions of the coupling elements from the dialysis bag are retained, when shipped, in sterile condition by being surrounded by a manually releasable cover formed as a pair of half-shells of plastic material, retaining therein a sponge material which is impregnated with a disinfectant solution, the sponge material compressing about and closely surrounding the fitting which is to be shipped in sterile manner. The two half-shells, for example, can be plastic, including a living hinge connecting them together, with snap or release openings at their free end, so that they can be readily snapped apart by the fingers of one hand, and permit sterile attachment of connection tubing to the outlet from the bag which, previously, was protected in sterile condition by the impregnated foam material within the half-shells.

DRAWINGS

FIG. 2 is a schematic top view of the dialysis bag;

Figure 1:
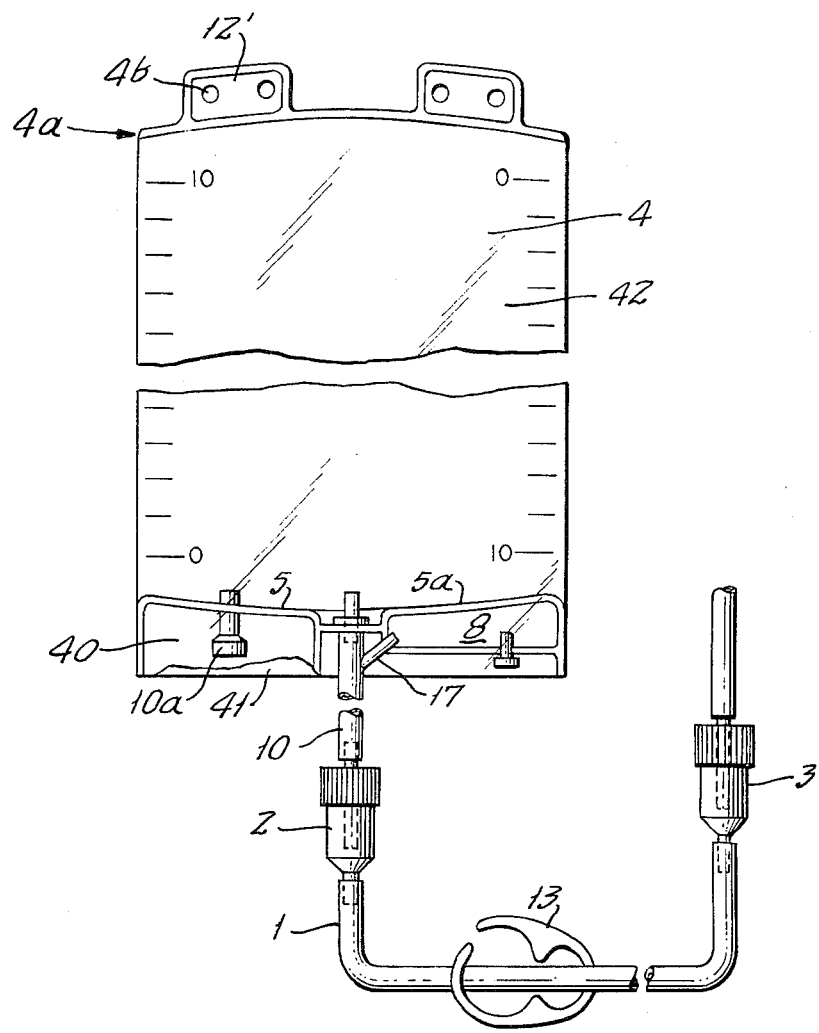
FIG. 1 illustrates, schematically, a dialysis bag and the dialysis system in accordance with the present invention.

The apparatus comprises a bag 4 made of two flat plane sheets of plastic, for example vinyl chloride polymer which, originally, can be cut from a tube. To close off the plastic, it is welded together at an upper edge portion 4a, and formed therein are suspension holes 4b, to permit suspending the bag from a suitable support. The shape of the end portion can be as illustrated in FIG. 1, with extending flaps 12′, or, as shown in FIG. 2, with cross seams 12a, or may have any other suitable form to permit suspending the bag from a hanger.

The sides of the bag, preferably, carry gradations which indicate the contents in milliliters, for example, and preferably in both ascending as well as descending order, so that the quantity in the bag, when the bag is emptied from full condition, can be determined, as well as the quantity which is placed into the bag, when it is used as a receptacle for contaminated dialysis fluid. Gradations may, also, be in percent of filling, as indicated in FIG. 1, or in absolute units, as indicated in FIG. 2.

The lower portion of the bag is subdivided by a seam line formed, for example, as a heat weld. The seam line 5 extends across the two sheets of vinyl chloride polymer 40, 41 forming the bag so as to define therein a dialysis fluid chamber 42. Access to the interior of the dialysis fluid chamber, for filling the same, is obtained by the plug 10a, constructed in well known form, and sealed between the sheet 40, 41 forming the bag 4. The plug 10a, for example, is a plastic tube, closed off at the end by a filler which may include a membrane, permitting insertion of a needle through the end portion to introduce dialysis saline solutions into the bag, withdrawal of the needle then sealing the plug 10a to maintain the contents within the chamber 42 in sterile condition.

The bag 4 is connected through an outflow tube 10 to a fitting 2 which, in turn, is connected to a tubular duct 1. The flow through the tubular duct 1 can be controlled by a flow control clamp 13, as well known in the medical fluid application field. The duct 1 is, in turn, connected to a fitting 3 which can in turn be connected to a catheter, for example permanently installed in the body of the patient (not shown) and for providing access to the peritoneal cavity. A suitable catheter is, for example, a Tenckoff catheter.

Figure 3:
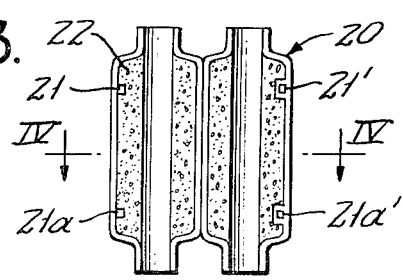
FIG. 3 is a front view of a sterility maintaining capsule.
Figure 4:
FIG. 4 is a cross-sectional view along line IV—IV of FIG. 3.

For shipment, the tube 1 and the fittings 2, 3 may be separate. In order to keep the end portion of the tube 1, 10 in sterile condition, and also in order to keep the fittings 2, 3 in sterile condition—if separated from the respective tubes to which they are attached—a sterile connecting jacket 20 (FIGS. 3, 4) is provided. The sterile jacket 20 is formed of two half-shells 21, 21'. The two half-shells, preferably of polyethylene, retain therein sponge material 22 which can be pre-shaped, at least approximately, to the shape of the fitting or tube element it is to receive. The sponge material 22 is for example polyurethane foam, and soaked with a disinfectant liquid of suitable type. The half-shells 21, 21' have interengaging latching elements 21a, 21a', for example in the form of pins projecting from one half-shell with a slightly oversized button fitting into a recess in the other half-shell; other arrangements, such as externally placed snap elements on one half-shell engaging over a ridge on the other, may be used. The half-shells, preferably, are connected by a living hinge. The latching elements 21a, 21a' should be so dimensioned and constructed that they firmly locate the sponge material about the tube fitting or the tube members to prevent contamination by the patient's hands, but permit snapping open by one hand, for sterile insertion of the end portion of the enclosed element into the respective tubing or fitting, or vice versa.

The outlet tube 10 is closed off by a releasable closing member 11. The outlet 10 is formed as a plastic tube 16, sealed into a seam or sealing portion 15 by heat welding the tube 16 to the seamed portion 15. A second tube 17 merges into the tube 16. The second tube 17 is in communication with a disinfectant liquid chamber 8 (FIG. 2). The disinfectant chamber 8, preferably, also is connected to the outside by a filler plug 18a, similar to the filler plug 10a. The filler plug 18a may be differently colored from the filler plug 10a to prevent mistakes when first filling the bag. Chamber 8 is much smaller than chamber 42.

The ducts 16 and 17 can be closed off to prevent drainage of fluid therefrom, when not desired, by closures 11, 19, respectively. Closure 11 is a plastic plug which has an extending pin 12, integral with a flange portion 13, closing off the interior of the tube 16. The junction line between the flange 13 and the pin 12 is such that, by moving the flexible walls 40, 41 back and forth, the pin 12 can be broken off from the flange 13, thus exposing the interior of the tube 16 to the chamber 42, and permitting flow of fluid therefrom. A similar closing plug can be used with duct 17. FIG. 2 illustrates, however, a further embodiment of the invention. Rather than using a frangible opening, a ball 19 is pressed into the end portion of the tube 17 before the tube 17 is assembled into the bag, by heat sealing the tube combination 16–17 into the seam line 5, and the continguous sealing portion 15. By squeezing the tube 17, just below the ball 19, the ball 19 can be expelled to assume the position 19' shown in FIG. 2, thus permitting flow of fluid from chamber 8 through the tube 17 into the tube 10, and hence into the connecting line 1 and through coupling 3 to the catheter implanted in the patient. Preferably, the ball 19 and the pin 12, or a pin corresponding to the pin 12 and connected to the end of tube 17, are of different color to assist the patient in use of the bag.

The bag incorporates, in one unit, a disinfectant container, that is the chamber 8, and the dialysis liquid chamber 42. The two sheet-like portions of the bag 4 extend at their lower end portion 9 in the form of open flaps 90, 91 which cover the liquid introducing plug 10a; similar flaps 90a, 91a can be provided to cover the plug 18a. Thus, the user will be protected against the circular projecting portions of the ends of the plugs or fittings 10a, 18a, and if they should bear against the body of the patient, no discomfort or rubbing thereof will be experienced.

The chamber 8, in initial use, is located in the lower portion of the bag 4, opposite to the inlet plug 10a. The small chamber 8 can be formed as a pocket in the flap or lip region of the bag, as best seen in FIG. 2, for example by thermal sealing, so that the respective flaps or lips of the bag, or at least one of them, will remain to lie beneath the fluid insertion plug 18a. The Y-shaped fitting formed by the tubes 16, 17 thus is concealed in the soft and protecting portion of the bag element itself, resulting in a compact construction with minimum discomfort to the user.

In use, the user will first open the protective sleeves or snap cover elements 20, connect fitting 2 to the tube 10, the line 1, with the clamp 13, if needed, to the fitting 2, and the other end of line 1 to the fitting 3 which, in turn, is to be connected to the non-sterile portion of the catheter implanted in the patient. Of course, if the tubing 10 is of sufficient length, a single fitting like fitting 2 or 3 suffices. The bag 4 then is suspended from the suspension holes 4b, the closure pin 12 broken and ball 19 expelled—or a pin similar to pin 12 communicating with duct 17 is broken—permitting introduction of the dialysis saline solution into the peritoneal cavity of the patient. the disinfectant liquid will leave the chamber 8, mix with the dialysis fluid, to permit introduction thereof.

Upon termination of the dialysis, the disinfectant sleeve 20 can be re-used to close off any remaining open tubing, which may not be clamped tight.

The draining step of the dialysis operation is carried out by lowering the then empty bag, for example by suspending it from holes 4c at a position below the peritoneal cavity of the patient, and permitting the used drainage fluid to flow thereinto. Of course, some of the fluid will fill into the chamber 8. This, however, is immaterial since the bag is intended to be disposable, with the contaminated fluid retained therein, for example by a clamp similar to clamp 13 being placed around the outflow tube 10. The disinfectant protective sleeve 20, about the end of the tube 10, or the fitting 2, as the case may be, can then be re-used.

A single bag, therefore, is provided for dialysis fluid, for the dialysis process and for draining, as well as for disinfection. The junction fitting for disinfectant and dialysis saline solution is part of the bag. This arrangement permits ambulatory use, and introduction of liquid into the patient's body, as well as draining therefrom, with the apparatus rolled up, and concealed under the patient's clothes; filling of the bag with disinfectant and dialysis fluid, for example from a separately carried container, can be carried out by the patient, under sterile conditions, by introducing disinfectant and dialysis saline solution respectively, through the penetrable fittings 18a, 10a.

The disinfectant dose in the inside of the chamber 8 will be effective to provide an efficient disinfecting agent without modifying the osmotic properties of the dialysis liquid. Thus, the disinfectant should be stored and retained separately from the dialysis liquid as such. This is accomplished in the bag by placing the chamber 8, as a separate heat seal chamber separated off from the main chamber by heat seal lines 5a to, in turn, receive its separate disinfectant liquid. A disinfectant liquid which has been found to be particularly effective is chlorexidine, which is effective against peritonitis.

Various modifications and changes may be made within the scope of the invention concept.

I claim:

1. Continuous peritoneal dialysis bag, adapted for connection to a catheter associated with the abdominal cavity of a patient, comprising
    a flexible bag (4) of heat soluble flexible plastic material, formed of two parallel plastic walls (40, 41) secured together at heat weld connection lines (4a, 5, 5a) to define therebetween a plurality of chambers (42, 8) and communication ducts (16, 17) sealed into said connection lines to provide for fluid communication with the chambers,
    wherein a first heat weld connection line (5) extends essentially transversely across the bag to define a dialysis fluid chamber (42) in the bag, and a second heat weld connection line (5a) is spaced from said first connection line to define a disinfectant chamber (8) in the bag;
    a first one (16) of the communication ducts extending from the dialysis fluid chamber (42) to the outside thereof;
    a second one of the communication ducts (17) extending from the disinfectant chamber (8) and merging into the first communication duct (16), to permit injection of disinfectant fluid from the disinfectant chamber into the first communication duct for fluid delivery from the dialysis chamber;
    a third communication duct (10a) extending from the outside of the bag into the dialysis chamber (42);
    a first manually releasable closure means (12, 13) closing off the inside of said first communication duct (16) within said dialysis fluid chamber (42);
    a second releasable closure means (19) closing off the inside of said second communication duct (17) located within the disinfectant chamber;
    and externally accessible closing means closing the third communication duct (10a).

2. Bag according to claim 1, wherein the communication ducts are plastic tubes sealed to the plastic material forming the bag.

3. Bag according to claim 1 wherein the plastic bag is defined by two parallel flat sheets of flexible plastic;
    the communication ducts are plastic tubes sealed to the sheets forming the walls of the bag along a portion of their length;
    and wherein the first and second ducts are joined at a junction located within the region of the seal of the communication ducts to the sheets.

4. Bag according to claim 1 further including a fourth closeable communication duct (181) communicating from the outside to the disinfectant chamber (8) and being externally accessible for introduction of disinfectant fluid therein.

5. Bag according to claim 1 wherein the plastic bag is defined by two flat sheets of flexible plastic have extending flap portions (90, 91, 90a, 91a) extending over at least the third closeable communication duct (10a) to form a protective flap over the terminal portion thereof and over the closure means thereof.

6. Bag according to claim 1, further including a cross seam portion (4a) forming a connection line remote from said first and second connections lines;
    suspension holes (4b) positioned adjacent said cross seam portion to permit suspension of the bag with the first and second communication ducts extending downwardly;
    and additional suspension holes (4c) formed in the flat sheet element adjacent said first and second communication ducts to permit suspension of the bag with at least said first communication duct (16) extending upwardly to permit drainage of fluid thereinto and into the dialysis chamber.

7. Bag according to claim 1, wherein said releasable closure means comprises a plug and a frangible pin element (12) closing off a through-opening through the plug, the pin element permitting breaking off of the pin by flexing of the pin by pressure on the flexible plastic bag, breaking of the pin at a break line of the pin with the plug, and thus establishing fluid communication from the interior of the respective chamber (42) with the exterior thereof.

8. Bag according to claim 1,
    wherein the releasable closure means of the communication ducts communicating with the dialysis chamber (42) and with the disinfectant chamber (8), respectively, are of different color to permit ready identification of the respective closure means;
    and wherein the flexible plastic material of the bag is sufficiently transparent to permit observation of the respective color.

9. Bag according to claim 1, wherein the first communication duct (10) has an end portion positioned outside of said bag;
    a tube coupling element (2) secured to the end portion;
    and further comprising, in accordance with the invention,
    manually releasable means (20) keeping the tube coupling element and the duct portion adjacent thereto in sterile condition, comprising
    a pair of half-shells (21, 21') of plastic material;
    a compressible foam material (22) located in the half-shells and essentially filling the half-shells;
    disinfectant solution retained and absorbed in the foam material within the half-shell;
    and releasable connection means (21a, 21a') securing the half-shells together, said half-shells being closed over the coupling element and the duct portion adjacent thereto to prevent external contamination thereof.

10. Bag according to claim 9, wherein the releasable connection means comprises a living hinge securing the half-shells (21, 21') together at one side, whereby said half-shells will form a single element;

and matching interengaging locking means (21a, 21a') formed on the respective ones of the half-shells at locations remote from the living hinge.

11. Bag according to claim 10, wherein the half-shells are elongated and formed with constricted half-tubular end sections fitting over the portions of the communication duct adjacent the coupling elements.

12. Bag according to claim 1, wherein said plastic bag is defined by two flat, flexible sheets; and the releasable closure means comprises a ball (19) frictionally retained within the communication duct and capable of being expelled upon pressure through the wall portions of the sheets of the bag and the wall portions of the respective communication duct.

* * * * *